United States Patent
Schwartz et al.

(10) Patent No.: US 10,806,424 B2
(45) Date of Patent: Oct. 20, 2020

(54) IMAGER WITH BUMP DETECTION (71) Applicant: VAREX IMAGING CORPORATION, Salt Lake City, UT (US)

(72) Inventors: Rudiger Schwartz, Sunnyvale, CA (US); Michelle Richmond, Palo Alto, CA (US); Maxwell Allen, Redwood City, CA (US); Isaias Job, San Jose, CA (US)

(73) Assignee: VAREX IMAGING CORPORATION, Salt Lake City, UT (US)

( * ) Notice: Subject to any disclaimer, the term of this patent is extended or adjusted under 35 U.S.C. 154(b) by 74 days.

(21) Appl. No.: 15/283,270

(22) Filed: Sep. 30, 2016

(65) Prior Publication Data
US 2018/0092617 A1 Apr. 5, 2018

(51) Int. Cl.
*A61B 6/00* (2006.01)
*A61B 6/03* (2006.01)

(52) U.S. Cl.
CPC .............. *A61B 6/54* (2013.01); *A61B 6/032* (2013.01); *A61B 6/4085* (2013.01);
(Continued)

(58) Field of Classification Search
CPC ..................................................... A61B 6/542
See application file for complete search history.

(56) References Cited

U.S. PATENT DOCUMENTS 6,972,411 B2 12/2005 Schick et al.
7,211,802 B1 5/2007 Dhurjaty et al.
(Continued)

FOREIGN PATENT DOCUMENTS

EP       2338418 A1   6/2011
JP     2011139851 A   7/2011
(Continued)

OTHER PUBLICATIONS

The Extended European Search Report, Application No. 17192850.0, dated Mar. 2, 2018.
(Continued)

*Primary Examiner* — Dani Fox
(74) *Attorney, Agent, or Firm* — Su IP Consulting (57) ABSTRACT

An example imaging device for generating an image is disclosed. The device may include an imaging detector array configured to collect charges during a radiation exposure at the imaging detector array. The device may include a signal generator coupled with the imaging detector array. The signal generator may be configured to generate a detection signal based on the charges collected by the imaging detector array. The device may include an accelerometer configured to generate an acceleration signal indicative of external forces applied to the imaging device. The device may further include a signal processor coupled with the signal generator and the accelerometer. In response to a determination that the acceleration signal is below a predetermined disturbance threshold and the detection signal exceeds a predetermined threshold, the signal processor may be configured to generate the image based on the detection signal.

14 Claims, 7 Drawing Sheets

(52) U.S. Cl.
CPC .......... *A61B 6/4208* (2013.01); *A61B 6/4233* (2013.01); *A61B 6/5205* (2013.01); *A61B 6/5294* (2013.01); *A61B 6/542* (2013.01)

(56) References Cited

U.S. PATENT DOCUMENTS

| | | |
|---|---|---|
| 8,358,740 B2 | 1/2013 | Nakatsugawa et al. |
| 8,513,616 B2 | 8/2013 | Desaute |
| 9,201,149 B2 | 12/2015 | Ben Hayun et al. |
| 9,320,482 B2 | 4/2016 | Tajima |
| 2008/0175353 A1 | 7/2008 | Durack |
| 2011/0170669 A1 | 7/2011 | Nakatsugawa et al. |
| 2012/0114099 A1* | 5/2012 | Yoshida ............... A61B 6/4233 378/62 |
| 2013/0259196 A1 | 10/2013 | Tajima |
| 2014/0348299 A1 | 11/2014 | Sung et al. |

FOREIGN PATENT DOCUMENTS

| | | |
|---|---|---|
| JP | 2012100807 A | 5/2012 |
| JP | 2013202057 A | 10/2013 |
| JP | 2015062012 A | 4/2015 |

OTHER PUBLICATIONS

Office Action (Notification of Reasons for Refusal), Application No. 2017-189971, dated Jul. 17, 2018, Japan Patent Office.

* cited by examiner

Figure 5 ated fluoroscopy modality, may need to know when an X-ray generator has become active in order to generate the resulting X-ray images. In the past, this was usually done by connecting a physical wire between the X-ray generator and the X-ray imager to transmit an active signal to the X-ray imager. In many situations, this physical wire is obtrusive, difficult to integrate, and subject to physical damage. As a result, the X-ray imager may need to actively detect the incoming X-rays.

IMAGER WITH BUMP DETECTION

BACKGROUND

Unless otherwise indicated herein, the approaches described in this section are not prior art to the claims in this application and are not admitted to be prior art by inclusion in this section.

An X-ray imager, operating either in a single-shot modality or a triggered fluoroscopy modality, may need to know when an X-ray generator has become active in order to generate the resulting X-ray images. In the past, this was usually done by connecting a physical wire between the X-ray generator and the X-ray imager to transmit an active signal to the X-ray imager. In many situations, this physical wire is obtrusive, difficult to integrate, and subject to physical damage. As a result, the X-ray imager may need to actively detect the incoming X-rays.

Physically bumping an X-ray imager may cause a microscopic flexing in an imaging detector array of the X-ray imager. This microscopic flexing may produce a microscopic signal which is unfortunately indistinguishable from the true X-ray detection signal generated based on incoming X-rays. Thus, the X-ray imager may generate useless X-ray images based on the microscopic flexing, or generate low-quality X-ray images that are greatly affected by the microscopic flexing.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated herein.

The present disclosure is related to systems and methods for supporting an auto-trigger circuit with bump detection in an imager, such as an X-ray imager. Specifically, embodiments of the present disclosure may utilize a high-speed accelerometer to detect external bumps. The accelerometer may generate an acceleration signal indicative of the presence of the external bumps, and the acceleration signal may be used to prevent the auto-trigger circuit from firing a false trigger. This allows the sensitivity of the auto-trigger circuit to be increased, while considerably reducing the minimum dose at which the X-ray imager may require in order to generate reliable X-ray images.

X-radiation is a form of electromagnetic radiation. Throughout this disclosure, the term "X-ray" is used to illustrate the examples, but it can be used interchangeably with "radiation." For example, an "X-ray image" can be referred to as a "radiation image," an "X-ray imager" can be referred to as a "radiation imager," and an "X-ray exposure" can be referred to as a "radiation exposure." In addition, the terms "imager," "imaging system," and "imaging device" are intended to cover various forms of imaging, such as, without limitation, X-ray imaging and magnetic resonance imaging (MRI). Unless otherwise defined, the term "or" can refer to a choice of alternatives (e.g., a disjunction operator, or an exclusive or) or a combination of the alternatives (e.g., a conjunction operator, and/or, a logical or, or a Boolean OR).

Figure 1:
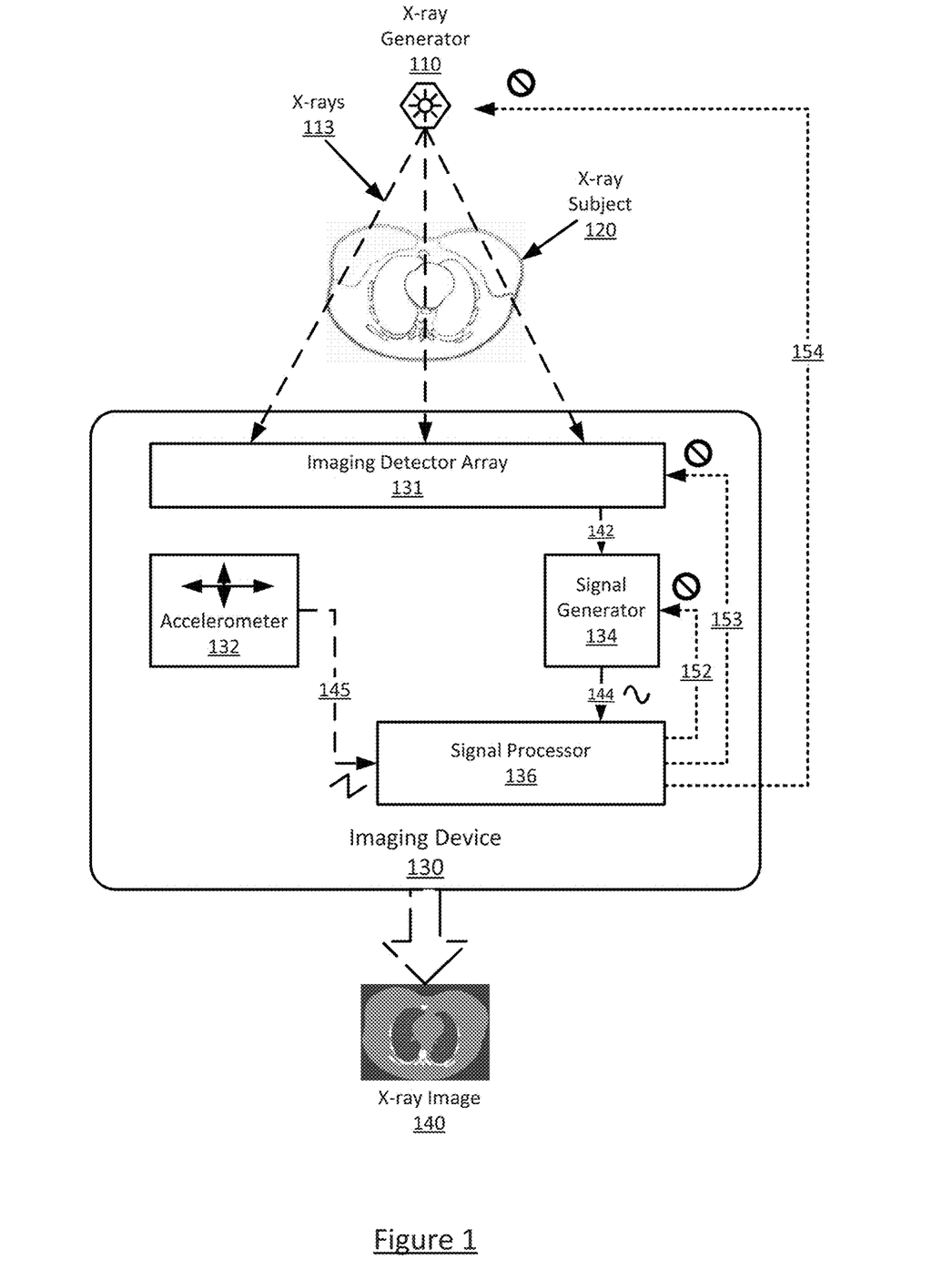
FIG. 1 shows a block diagram illustrating a imaging system configured with bump detection.

FIG. 1 shows a block diagram illustrating an imaging system configured with bump detection, in accordance with certain embodiments of the present disclosure. In FIG. 1, the imaging system may include, among other hardware components, an X-ray generator 110 (e.g., an X-ray tube powered by a tube generator) and an imaging device 130 (e.g., an X-ray imager). During an X-ray examination, an X-ray subject 120 (e.g., a patient) may be placed between the X-ray generator 110 and the imaging device 130. The X-ray generator 110 may be configured to direct the generated X-rays 113 toward the X-ray subject 120 and the imaging device 130. Based on the X-rays 113 that reached the imaging device 130, the imaging device 130 may be configured to generate an X-ray image 140 associated with the X-ray subject 120.

In some embodiments, the X-ray generator 110 may be a device configured to emit one or more pulses of X-rays 113 at a particular angle/direction. The emitted X-rays 113 may be cone-beam, pencil-beam, and/or fan-beam photons with wavelengths across a particular spectrum. When the X-ray generator 110 projects X-rays 113 toward the X-ray subject 120, the photons of the X-rays 113 may interact with the X-ray subject 120. For the photons travelling toward the imaging device 130, some may pass through the X-ray subject 120, while others may be absorbed or deflected by the X-ray subject 120. Those photons of the X-rays 113 that eventually arrive at and are collected by the imaging device 130 may be collectively referred to as an "X-ray exposure."

In some embodiments, the imaging device 130 may also be referred to as, without limitation, a medical imaging device, an X-ray imager, an X-ray device, a computed tomography (CT) device, a cone-beam CT (CBCT) device, an industrial imager, or others. The X-ray image 140 may include 2-dimension (2D) or 3-dimension (3D) medical data generated by the imaging device 130. In some embodiments, the imaging device 130 may be a portable device that is detached from the X-ray generator 110. In other words, the imaging device 130 may be physically separated from the X-ray generator 110, may not be directly connected via a physical connection, and can only rely on itself to determine whether the X-ray generator 110 is emitting X-rays 113 or not. In other embodiments, the imaging device 130 and the X-ray generator 110 may communicate with each other via wireless communication means (e.g., WiFi®, Institute of Electrical and Electronics Engineers (IEEE) 802.11 standard, Bluetooth®, or IEEE 802.15 wireless communication standard).

In some embodiments, the imaging device 130 may include, among other hardware components, an imaging detector array 131, an accelerometer 132, a signal generator 134, and a signal processor 136. The imaging device 130 may contain additional hardware components which are not shown in FIG. 1, such as a current detector, a memory, a display screen, input keyboards, mouse, touchpad, touchscreen, light emitting diode (LED), buttons, or power supplies.

In some embodiments, the imaging detector array 131 may contain a pixel array having multiple pixels arranged into columns and rows. The imaging detector array 131 may be configured to sense and accumulate those X-rays 113 photons that reached the pixel array during an X-ray examination. Each pixel in the pixel array may include a photodiode sensitive to the X-rays 113, and a capacitor for accumulating an electric charge ("charge" or "electric current") generated by the photodiode sensing the X-rays 113. For each pixel in the pixel array, the higher dose of X-rays 113 (i.e., amount of X-ray exposure) that reaches its photodiode, the higher amount of charge is accumulated in its capacitor. After a predetermined time period which may last longer than the X-ray exposure, the pixels in the imaging detector array 131 may have collected/accumulated various charges that correspond to the amount and distribution of the X-rays that have passed through the X-ray subject 120 and reached the imaging detector array 131.

In some embodiments, the signal generator 134 may be configured to generate an X-ray detection signal based on the charges collected by the imaging detector array 131. The signal generator 134 may "read out" (142) the pixel array in the imaging detector array 131 by accessing each of the pixels in the pixel array either row-by-row or column-by-column. In other words, during the read-out process, the signal generator 134 may generate the X-ray detection signal with the accumulated charges of these pixels. The X-ray detection signal may subsequently be transmitted to the signal processor 136 for the constructing of an X-ray image 140. After the reading out of the pixel array and the generating of the X-ray detection signal, the signal generator 134 may discharge the currents accumulated in the pixel array, in order to prepare the imaging detector array 131 for the collecting of charges from subsequent X-ray exposures.

In some embodiments, the signal processor 136 may be a circuitry configured to control the overall operations of the imaging device 130. Specifically, the signal processor 136 may control the imaging detector array 131 and the signal generator 134 during the above generating of X-ray detection signal. The signal processor 136 may be further configured to switch between different power modes and perform bump detections, as described below.

In some embodiments, the signal processor 136 may configure an "X-ray threshold" with a predetermined intensity level for evaluating the existence of the X-ray detection signal generated by the signal generator 134. In other words, when the X-ray detection signal received by the signal processor 136 equals or exceeds the X-ray threshold, it means the intensity level of the X-ray detection signal exceeds the predetermined intensity level of the X-ray threshold, and the signal processor 136 may determine that there is X-ray detection signal being transmitted from the signal generator 134. When the X-ray detection signal received by the signal processor 136 is below the X-ray threshold, the signal processor 136 may determine that there is no X-ray detection signal being transmitted from the signal generator 134.

In some embodiments, the signal processor 136 may be implemented by a central processing unit (CPU) configured to execute software or firmware stored in the memory 135. The signal processor 136 may also be implemented, or may include, one or more programmable general-purpose or special-purpose microprocessors, digital signal processors (DSPs), programmable controllers, application specific integrated circuits (ASICs), programmable logic devices (PLDs), graphical processing units (GPUs) or the like, or a combination of such devices.

In some embodiments, the imaging device 130 may be configured to operate in a "full-power mode" or a "low-power mode." When the imaging device 130 is initially turned on, it may be placed in a low-power mode. Specifically, in the low-power mode, not all the components in the imaging device 130 are operating at full power. For example, the imaging detector array 131 may be operational, while the signal generator 134 and/or the signal processor 136 may be in a standby mode (with low power consumption) or an idle mode (turned-off).

In some embodiments, during the full-power mode, the signal generator 134 may read out the imaging detector array 131 and generate the X-ray detection signal, and the signal processor 136 may generate an X-ray image 140 based on the X-ray detection signal. Afterward, the signal processor 136 may be configured to switch the imaging device 130 back to the low-power mode. In some other situations, such as when a user of the imaging device 130 indicates that the X-ray capturing session is complete, the imaging device is configured to enter the low-power mode.

In some embodiments, the imaging device 130 may experience external physical bumps or movement during its usages. Especially in veterinary applications, the imaging device 130 as well as the X-ray generator 110 may be constantly in motion because the animal cannot stay still or the animal bumps the imaging device 130. In this case, the imaging device 130 may be subject to external forces, which may produce a microscopic flexing in its imaging detector array 131. This microscopic flexing may produce a microscopic signal which may unfortunately be indistinguishable from the X-ray detection signal generated based on an X-ray exposure. Thus, the signal generator 134 may mistakenly treat the microscopic flexing in the imaging detector array 131 as an X-ray exposure, and may falsely read out the imaging detector array 131 and generate a misleading X-ray detection signal and/or blurry X-ray image.

In some embodiments, the imaging device 130 may be implemented with an accelerometer 132 to detect any external physical bumps to the imaging device 130. The accelerometer 132 may be an electromechanical module configured to measure the existence and orientation of external forces caused by gravity, movement, or vibration. The accelerometer 132 may have two or three axes for determining the directions of the external forces in 2-dimensional or 3-dimensional coordination. During operation, the accelerometer 132 may output (145) an analog or digital "acceleration signal" indicative of the existence of the external forces applied to the imaging device 130. A high-sensitive accelerometer 132 with broad bandwidth may be utilized to generate accurate and reliable acceleration signals.

In some embodiments, the signal processor 136 may establish a "disturbance threshold" with a predetermined intensity level that is below the intensity level of the acceleration signal generated by the accelerometer 132 during a typical external bump which could affect the operations of the imaging device 130. When the acceleration signal received by the signal processor 136 equals to or exceeds the disturbance threshold (i.e., the intensity level of the acceleration signal equals to or exceeds the predetermined intensity level indicated by the disturbance threshold), the signal processor 136 may determine that the imaging device 130 is being bumped by external forces. On the other hand, when the acceleration signal received by the signal processor 136 is below the disturbance threshold (i.e., the intensity level of the acceleration signal is below the predetermined intensity level indicated by the disturbance threshold), the signal processor 136 may determine that no external bump to the imaging device 130 has occurred.

In some embodiments, the disturbance threshold which is compared with an acceleration signal generated by the accelerometer 132 may have a value that is at least 500 milli-gravitational force (mG). Gravitational force or g-force (G) is a unit of acceleration related to standard gravity or the Earth's gravity. In another embodiment, the disturbance threshold may have a value that is at least 250 mG. In yet another embodiment, the disturbance threshold may have a value within a range of 250 mG to 2 Gs, with an accelerometer resolution range of 100 mG to 500 mG. A disturbance threshold below 250 mG may be subject to noise from the accelerometer 132.

In some embodiments, in response to a determination that the acceleration signal exceeds the predetermined disturbance threshold, the signal processor 136 may generate one or more interrupt signals, and transmit these interrupt signals to various recipient components (e.g., imaging detector array 131, or signal generator 134) in the imaging device 130. An "interrupt signal" may be an analog or digital signal used to inform/instruct the recipient component to temporarily stop/interrupt its normal operations for a certain time period.

While the disturbance threshold discussed above is primarily compared to a magnitude of the acceleration signal, the phase and/or frequency information of the acceleration signal may be used to identify an external bump to the imager.

One example time period may correspond to when the external bumps stop before resuming normal operations. Another example time period may be configurable based on a typical period of time that the external bumps may last. In an embodiment, the interrupt stops normal operations for 1 millisecond (ms) to 100 ms. In another embodiment, the interrupt is cleared after predetermined duration of time or a fixed amount of time (e.g., in a range of 1-100 ms). In some examples, the interrupt signal can be referred to as a "blank signal" or "blanking signal" when the interrupt signal blocks, prevents, delays, or otherwise stops recipient components from generating an X-ray image.

In some embodiments, the signal processor 136 may transmit (152) an interrupt signal to the signal generator 134, informing it to temporarily stop its generating of X-ray detection signal for a fixed amount of time. The signal processor 136 may transmit (153) another interrupt signal to the imaging detector array 131, informing it to temporarily stop collecting charges from its pixel array. The signal processor 136 may optionally stop its own operation to generate X-ray image 140 based on X-ray detection signal.

In some embodiments, if any of the above hardware components is operating in a high-power mode, the signal processor 136 may also switch them to a low-power mode after they received the interrupt signals. Once the fixed amount of time elapses, the signal processor 136 may transmit a "resume signal" to these hardware components, informing them to resume their normal operations. Further, the imaging device 130 may contain an indicator (e.g., a speaker, a light, a LED, a display, or a message), which may be activated by the accelerometer 132 using the acceleration signal or the signal processor 136 using the interrupt signal. The indicator may let a user know when the interrupt signal has been generated (e.g., when the imaging device has been bumped and is unavailable to generate the X-ray image) or when the interrupt signal has been cleared. The indicator may also inform the user that the fixed amount of time has elapsed, or a resume signal has been transmitted (e.g., once the imaging device becomes available to generate the X-ray image).

Thus, the above approaches may decrease the amount of electricity consumed by imaging device 130 when performing various operations under physical bumps, thereby greatly reducing the power assumption of the imaging device 130, prolonging battery life, and allowing for a potentially smaller battery and lighter imaging device 130. The above approaches may also reduce the number of distorted images (e.g., distorted or blurry images) generated due to physical bumps.

In some embodiments, in response to a detection of any external bumps, the signal processor 136 may be configured to transmit (154) an interrupt signal to the X-ray generator 110 via wired, wireless, or optical communication. Once the X-ray generator 110 receives this interrupt signal, if the X-ray generator 110 is in the process of emitting X-rays 113, the X-ray generator 110 may temporarily stop its X-ray emission. Since in the presence of external bumps, the X-rays cannot be used to generate the X-ray image 140, any X-rays 113 emitted when there are external bumps can be harmful to the patient undergoing X-ray examination. Thus, the above approach may further reduce the X-rays dosages to minimum intensity determined based on the sensitivity of the imaging circuitry, not determined based on the external bumps.

Figure 2:
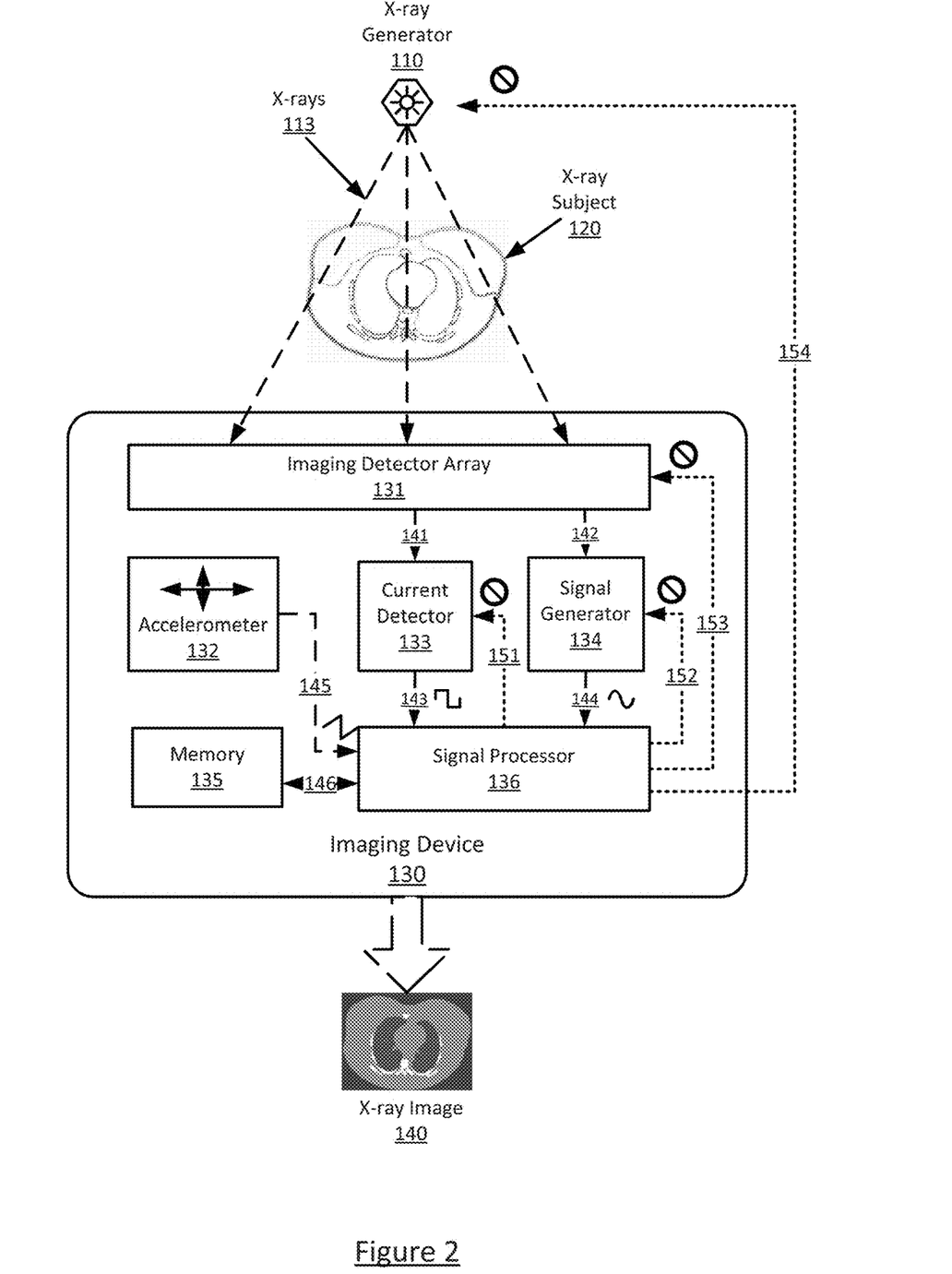
FIG. 2 shows a block diagram illustrating an imaging system configured with auto-triggering and bump detection.

FIG. 2 shows a block diagram illustrating an imaging system configured with auto-triggering bump detection, in accordance with certain embodiments of the present disclosure. In FIG. 2, the imaging system may include an X-ray generator 110 and an imaging device 130. The X-ray generator 110, the imaging device 130, as well as the components contained therein, correspond to their respective counterparts in FIG. 1. Further, the imaging device 130 of FIG. 2 may contain additional hardware components that are not shown in FIG. 1. Specifically, the imaging device 130 may include, among other hardware components already shown in FIG. 1, a current detector 133, and a memory 135.

In some embodiments, the current detector 133 may be an auto-trigger circuitry configured to provide X-ray sensing functions to the imaging device 130. The current detector 133 may generate a "triggering signal" indicative of the existence of an X-ray exposure at the imaging detector array. Specifically, the current detector 133 may monitor and detect (141) the fluctuations of the electric currents flowing through the imaging detector array 131, and continuously generate "electric current outputs" associated with the imaging detector array 131 by reading the charges accumulated in the pixel array of the imaging detector array 131 during the X-ray exposure.

U.S. Pat. No. 6,972,411 entitled, "Method of Event Detection for Intraoral Image Sensor," U.S. Pat. No. 7,211,802 entitled, "X-ray Impingement Event Detection System and Method for a Digital Radiography Detector," and U.S. Pat.

No. 8,513,616 entitled, "Radiographic Imaging Device and a Detector for a Radiographic Imaging Device," U.S. Pat. No. 9,201,149 entitled, "X-ray Radiation Detector with Automatic Exposure Control," which are incorporated by reference in their entirety, disclose examples of auto-trigger circuitry.

In some embodiments, the current detector 133 may include a comparator to compare the electric current outputs of the imaging detector array 131 with a predetermined "X-ray detection threshold." The X-ray detection threshold may be used to determine whether any X-rays 113 reached the imaging detector array 131. When the electric current outputs exceed the predetermined X-ray detection threshold, the current detector 133 may generate a "triggering signal" indicative of the existence of X-ray exposure at the imaging detector array 131. Afterward, the current detector 133 may transmit (143) the triggering signal to the signal processor 136, thereby "triggering" the signal generator 134 to initiate the generating of X-ray detection signal. Alternatively, the current detector 133 may optionally transmit the triggering signal directly to the signal generator 134, thereby triggering its X-ray detection signal generation process.

In some embodiments, in response to a triggering signal originated from the current detector 133, the signal generator 134 may be configured to generate an X-ray detection signal based on the charges collected by the imaging detector array 131. After being triggered, the signal generator 134 may read-out (142) the pixel array in the imaging detector array 131 and generate an X-ray detection signal including the accumulated charges of these pixels. The X-ray detection signal may subsequently be transmitted to the signal processor 136 for the constructing of an X-ray image 140.

In some embodiments, the signal processor 136 may control the imaging detector array 131, the current detector 133, and the signal generator 134 during the above auto-sensing of the X-ray exposure and the generating of X-ray detection signal. Further, in response to the triggering signal transmitted (143) from the current detector 133, the signal processor 136 may transmit a triggering signal to the signal generator 134 to initiate the reading-out of the imaging detector array 131 and the generating of the X-ray detection signal. The signal processor 136 may be further configured to switch between different power modes and perform bump detections, as described below.

In some embodiments, the memory 135 may represent any form of random access memory (RAM), read-only memory (ROM), flash memory, cache memory, or a combination of such devices. For example, the X-ray image 140 generated by the signal processor 136 may be stored (146) in the memory 135. And the X-ray image 140 may be subsequently retrieved from the memory 135 for transmitting to an external computer. During operation, the memory 135 may contain, among other things, a set of non-transitory machine-readable instructions which, when executed by the signal processor 136, causing the signal processor 136 to perform at least some embodiments of the present disclosure.

In some embodiments, during the low-power mode, the current detector 133 may continuously monitor the imaging detector array 131 for any X-ray exposure. Upon detecting onset of X-ray exposure at the imaging detector array 131, the current detector 133 may transmit (143) a triggering signal to the signal generator 134 and/or the signal processor 136, which may wake-up the signal generator 134 and the signal processor 136 to operate at full power, and may cause all other components in the imaging device 130 to be switched to the full-power mode.

In some embodiments, during the full-power mode, the signal generator 134 may read out the imaging detector array 131 and generate the X-ray detection signal in response to the triggering signal, and the signal processor 136 may generate an X-ray image 140 based on the X-ray detection signal. Afterward, the signal processor 136 may be configured to switch the imaging device 130 back to the low-power mode, leaving the current detector 133 to continuously monitor further X-ray exposure.

In some embodiments, the imaging device 130 may experience external physical bumps or movement during its usages, which may produce a microscopic flexing in its imaging detector array 131. This microscopic flexing may produce a microscopic signal which may unfortunately be indistinguishable from the X-ray detection signal generated based on an X-ray exposure. Thus, the current detector 133 may mistakenly treat the microscopic flexing in the imaging detector array 131 as an X-ray exposure, and may falsely trigger the signal generator 134 to read out the imaging detector array 131 and generate a misleading X-ray detection signal and/or blurry X-ray image.

In some embodiments, in response to a determination that the acceleration signal exceeds the predetermined disturbance threshold, the signal processor 136 may generate one or more interrupt signals, and transmit these interrupt signals to various recipient components (e.g., imaging detector array 131, current detector 133, or signal generator 134) in the imaging device 130.

In some embodiments, the signal processor 136 may transmit (151) one interrupt signal to the current detector 133, informing it to temporarily stop its detecting of X-ray exposure in the imaging detector array 131 and stop generating the triggering signal for a fixed amount of time. In other words, the interrupt signal may be used to prevent the current detector 133 from triggering the signal generator 134 to initiate the generation of the X-ray detection signal. Alternatively, the interrupt signal may be used to delay (e.g., for a duration of typical external bumps) the current detector 133 from initiating the generation of the X-ray detection signal by the signal generator 134. In other embodiments, the signal processor 136 may delay the trigger signal by a predetermined delay time (e.g., 100 microseconds (µs) to 1 ms) to allow the accelerometer 132 to generate the acceleration signal.

Further, by having the accelerometer 132 to detect external bumps, the imaging detector array 131 may not collect false charges, and the current detector 133 may not need to set up a high level of "X-ray detection threshold" to rule out the disturbance caused by the external bumps. As a result, the X-ray detection threshold can be lowered to a level that is determined based on the X-ray dosage necessary for the generation of the X-ray image 140. For example, the X-ray generator may adjust a duration or intensity of the X-ray exposure based on a sensitivity of pixels in the imaging detector array 131 or delays by the signal processor 136. Thus, the intensity and the duration of the X-rays 113 emitted by the X-ray generator 110 and number of X-ray images taken may be greatly reduced, thereby providing a safer X-ray examination for the patient.

Figure 3:
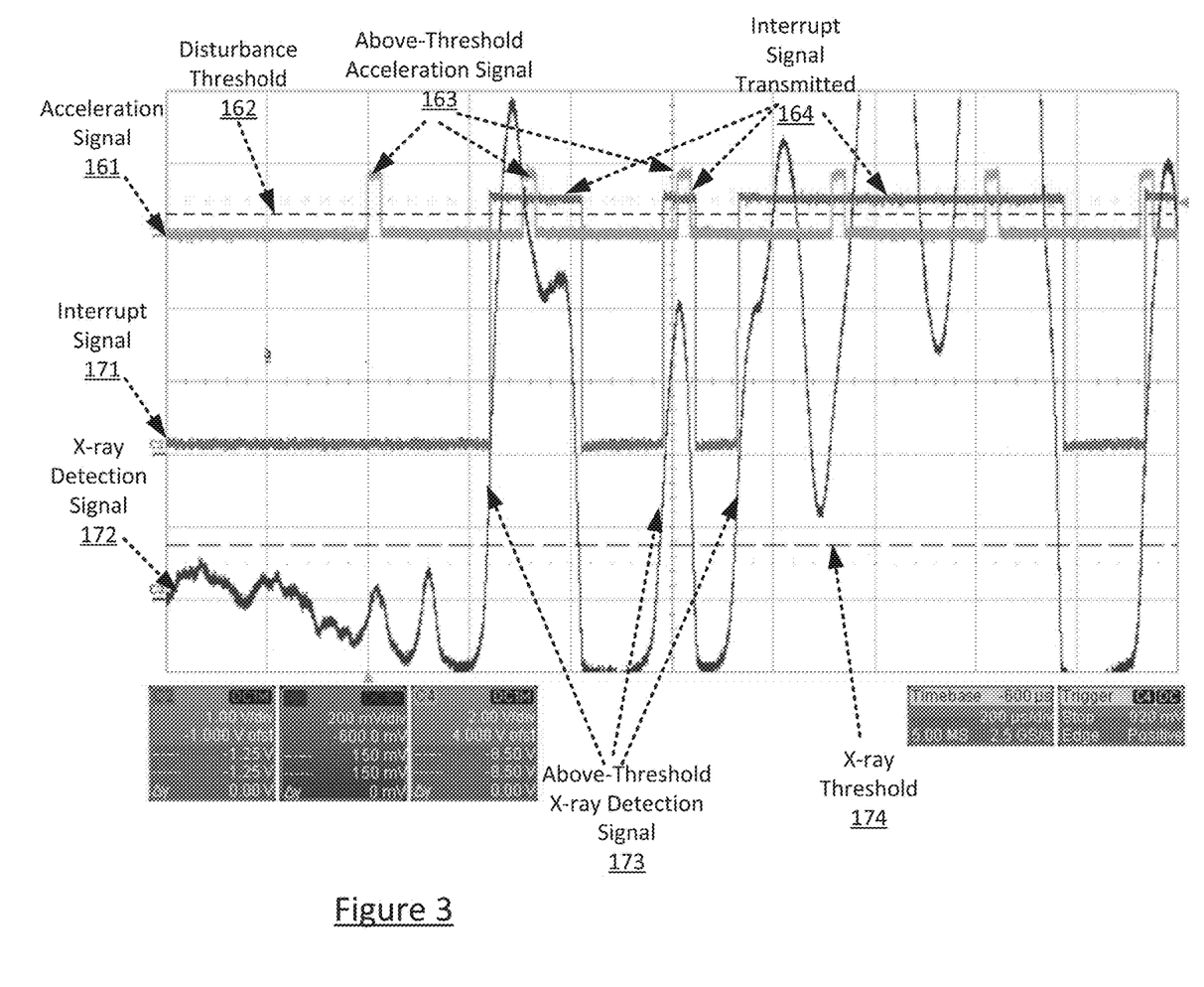
FIG. 3 illustrates a diagram showing various signals and thresholds.

FIG. 3 illustrates a diagram showing various signals and thresholds, in accordance with certain embodiments of the present disclosure. FIG. 3 shows an acceleration signal 161 generated by an accelerometer of an imaging device, an X-ray detection signal 172 generated by a signal generator of the imaging device, and an interrupt signal 171 generated by a signal processor of the imaging device, all throughout a same period. FIG. 3 may include a disturbance threshold 162 for comparing with the acceleration signal 161, and an X-ray threshold 174 for comparing with the X-ray detection signal 172.

In some embodiments, the imaging device may experience external bumps during X-ray image generation. During the physical bumps, the acceleration signals 161 generated by the accelerometer may increase to a level that exceeds the disturbance threshold 162, becoming the illustrated above-threshold acceleration signals 163. At the same time, with the above-threshold acceleration signals 163, the X-ray detection signal 172 generated by the signal generator may also increase to a level that exceeds the X-ray threshold 174, becoming the illustrated above-threshold X-ray detection signals 173. Thus, based on the disturbance threshold 162, the signal processor may be able to differentiate between the X-ray detection signals that are caused by external bumps or generated based on incoming X-rays.

In some embodiments, in view of the above-threshold acceleration signals 163 and the above-threshold X-ray detection signals 173, the signal processor may generate a corresponding interrupt signals 164, and use these interrupt signals 164 to stop various components in the imaging device from generating useless data.

Figure 4A:
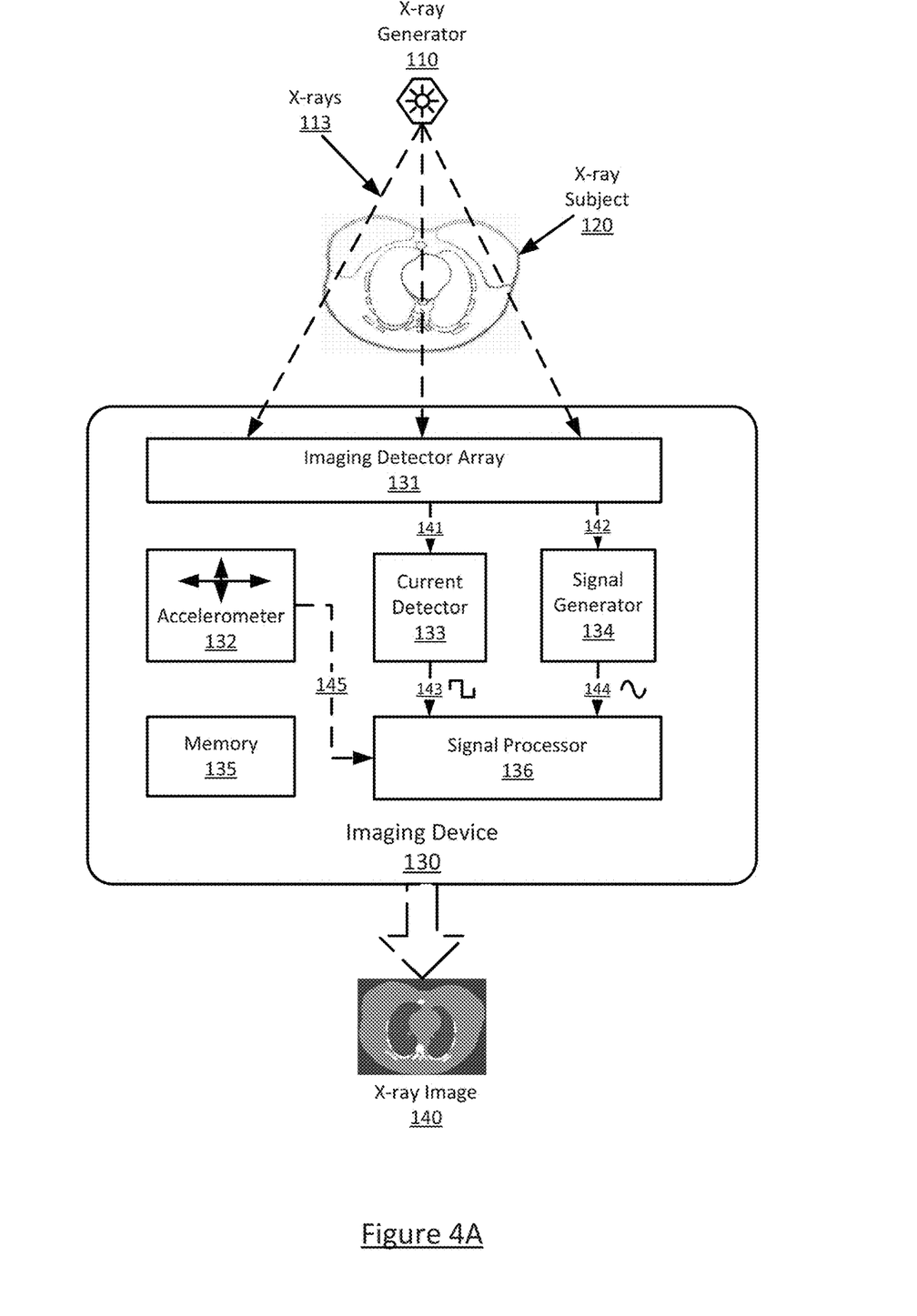
FIG. 4A illustrates an imaging device with bump detection during a normal operation.

FIG. 4A illustrates an imaging device with bump detection during a normal operation (e.g., without an external bump), in accordance with certain embodiments of the present disclosure. In FIG. 4A, the imaging device 130 as well as the various components and data flow arrows contained therein correspond to their respective counterparts in FIG. 2. Further, FIG. 4A shows a normal operation scenario in which the X-ray generator 110 and the imaging device 130 are in the process of performing an X-ray examination without external bumps.

In some embodiments, during an X-ray examination, in response to a determination that the acceleration signal generated by the accelerometer 132 is below the disturbance threshold, the signal processor 136 may determine that there is no external bumps. In this case, the imaging detector array 131 may be powered up to collect charges from the X-rays 113; the current detector 133 may continuously monitor and detect (141) the existence of the X-rays exposure at the imaging detector array 131; in response to a detection of the X-ray exposure by the current detector 133, the signal generator 134 may be triggered (143) to generate an X-ray detection signal by reading-out (142) the pixel array of the imaging detector array 131; and the signal processor 136 may generate an X-ray image 140 based on the X-ray detection signal received (144) from the signal generator 134.

Figure 4B:
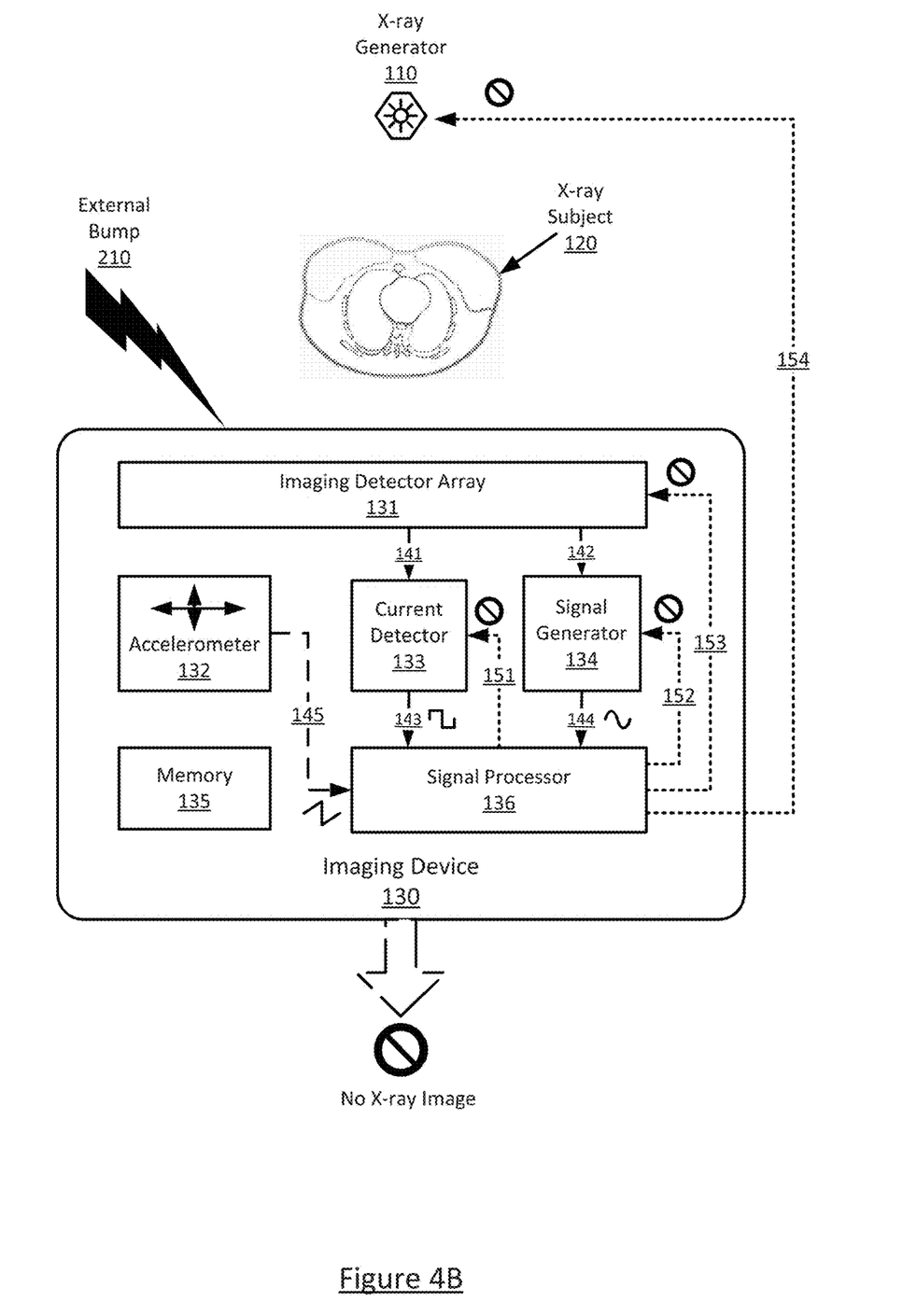
FIG. 4B illustrates an imaging device with bump detection undergoing an external bump during a standby operation.

FIG. 4B illustrates an imaging device with bump detection undergoing an external bump during a standby operation, in accordance with certain embodiments of the present disclosure. In FIG. 4B, the imaging device 130, as well as the various components and data flow arrows contained therein, correspond to their respective counterparts in FIG. 2. Further, FIG. 4B shows a standby operation scenario in which the X-ray generator 110 is not emitting X-rays and the imaging device 130 may be in a standby mode while encountering external bumps 210.

In some embodiments, during an X-ray examination, in response to a determination that the acceleration signal generated by the accelerometer 132 exceeds the disturbance threshold, the signal processor 136 may determine that there are external bumps 210. However, the imaging detector array 131 may still be powered up to collect charges from the X-rays 113; the current detector 133 may continuously monitor and detect (141) the existence of the X-rays exposure at the imaging detector array 131. Since the external bumps 210 may cause a microscopic flexing in the imaging detector array 131, the current detector 133 may mistakenly detect a nonexistence X-ray exposure, and may generate a triggering signal (143) to trigger the signal generator 134. Therefore, without the acceleration signal from the accelerometer 132, the signal generator 134 may generate a microscopic signal caused by external bumps, and the signal processor 136 may end up generating a useless X-ray image 140 based on the microscopic signal.

In some embodiments, in response to a detection of any external bumps 210, the signal processor 136 may transmit (151) one interrupt signal to the current detector 133, informing it to temporarily stop its detecting of X-ray exposure in the imaging detector array 131 and stop generating the triggering signal for a fixed amount of time. In other words, the interrupt signal may be used to prevent the current detector 133 from initiating the generation of the X-ray detection signal by the signal generator 134. Alternatively, the interrupt signal may be used to delay (e.g., for a duration of typical external bumps) the current detector 133 from initiating the generation of the X-ray detection signal by the signal generator 134. The signal processor 136 may transmit (152) another interrupt signal to the signal generator 134, informing it to temporarily stop its generating of the X-ray detection signal for a fixed amount of time. The signal processor 136 may further transmit (153) an interrupt signal to the imaging detector array 131, informing it to temporarily stop collecting charges from its pixel array. In some embodiments, the signal processor 136 may be configured to transmit (154) an interrupt signal to the X-ray generator 110 via wireless communication, to temporarily stop the X-ray generator 110 from emitting X-rays 113 for a fixed amount of time.

Figure 4C:
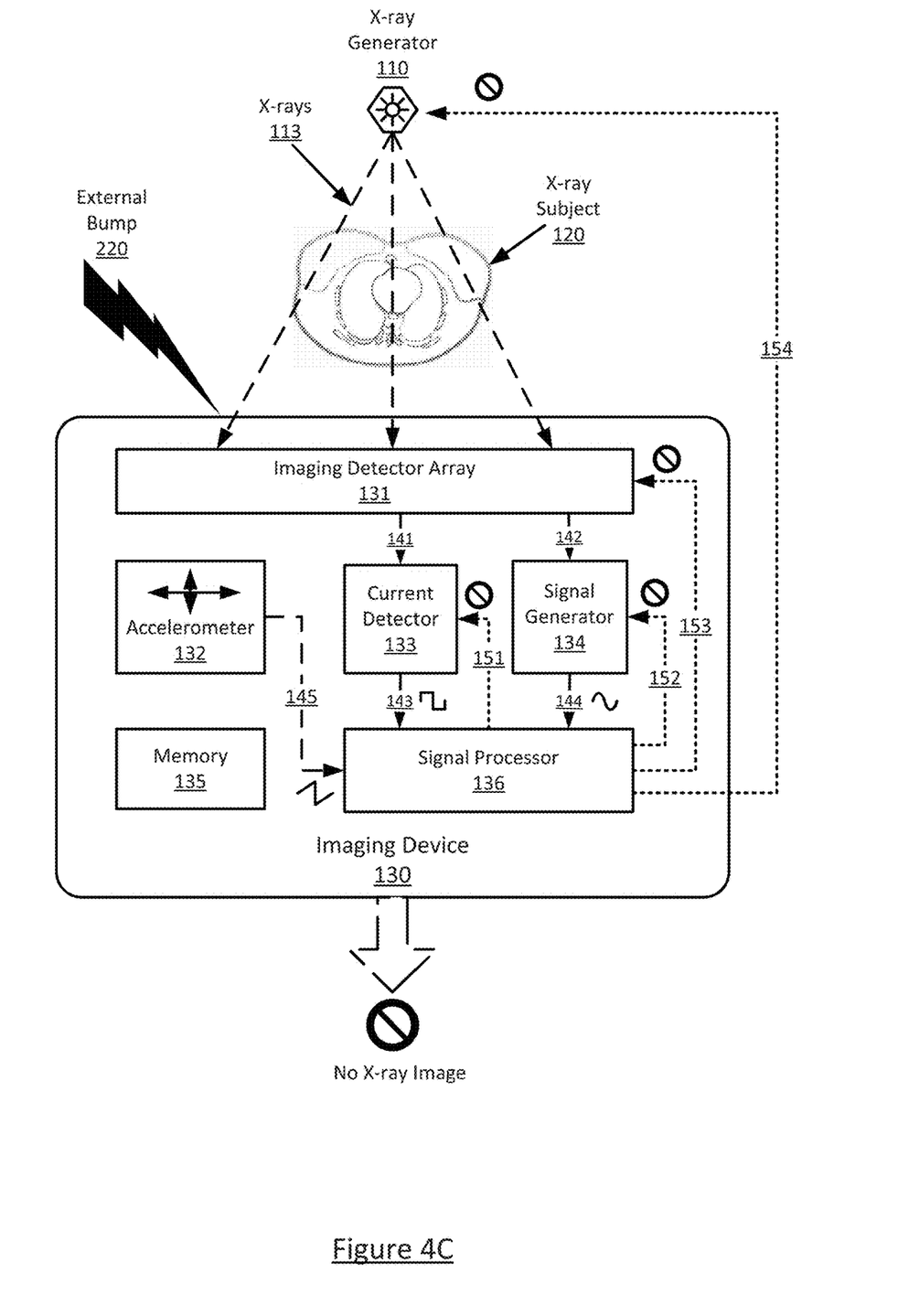
FIG. 4C illustrates an imaging device with bump detection undergoing an external bump during an X-ray exposure.

FIG. 4C illustrates an imaging device with bump detection undergoing an external bump during an X-ray exposure, in accordance with certain embodiments of the present disclosure. In FIG. 4C, the imaging device 130 as well as the various components and data flow arrows contained therein correspond to their respective counterparts in FIG. 2. Further, FIG. 4C shows a full-power operation scenario in which the X-ray generator 110 is emitting X-rays 113 and the imaging device 130 is capturing an X-ray image 140, while external bumps 220 may occur during the above process.

In some embodiments, during an X-ray examination, in response to a determination that the acceleration signal generated by the accelerometer 132 exceeds the disturbance threshold, the signal processor 136 may determine that there are external bumps 220. However, when the external bumps 220 occur, the imaging detector array 131 may be in the middle of collecting charges from the X-rays 113; the current detector 133 may be in the process of monitoring and detecting (141) the X-rays exposure at the imaging detector array 131; or the signal processor 136 may be in-route to generate the X-ray image 140 based on the X-ray detection signal. In the meantime, the X-ray generator 110 may still continuously emitting X-rays toward the patient. Therefore, the signal processor 136 may need to transmit interrupt signals to each of these components in order to stop the imaging device 140 from wasting its resources, and prevent the patient from being exposed to unnecessary X-ray radiation.

In some embodiments, since the external bumps 220 may cause a microscopic flexing in the imaging detector array 131, the pixels in the imaging detector array 131 may be filled with charges that are the combined results of the X-ray exposure and the microscopic flexing. As a result, even though the current detector 133 may "somewhat correctly" detect the X-ray exposure, and may generate a triggering signal to trigger the signal generator 134. However, the signal generator 134 may be triggered (143) to read-out (142) the pixel array of the imaging detector array 131, and output (144) an X-ray detection signal that is filled with noises caused by the external bumps 220. Thus, without the acceleration signal from the accelerometer 132 to signify the external bumps 220, the signal processor 136 may end up generating a useless X-ray image 140 (e.g., distorted or blurry image) based on the X-ray detection signal that is adversely affected by external bumps 220.

In some embodiments, in response to a detection of external bumps 220, the signal processor 136 may transmit (151) one interrupt signal to the current detector 133, informing it to temporarily stop its detecting of X-ray exposure in the imaging detector array 131 and stop generating the triggering signal for a fixed amount of time. In other words, the interrupt signal may be used to prevent the current detector 133 from triggering the signal generator 134 to initiate the generation of the X-ray detection signal. Alternatively, the interrupt signal may be used to delay (e.g., for a duration of typical external bumps) the current detector 133 from initiating the generation of the X-ray detection signal by the signal generator 134. The signal processor 136 may transmit (152) another interrupt signal to the signal generator 134, informing it to temporarily stop its generating of the X-ray detection signal for a fixed amount of time. The signal processor 136 may further transmit (153) an interrupt signal to the imaging detector array 131, informing it to temporarily stop collecting charges from its pixel array. In some embodiments, the signal processor 136 may be configured to transmit (154) an interrupt signal to the X-ray generator 110 via wireless communication, to temporarily stop the X-ray generator 110 from emitting X-rays 113 for a fixed amount of time. The signal processor 136 may also stop its own process of generating X-ray image 140 based on the X-ray detection signal that is adversely affected by external bumps 220.

Figure 5:
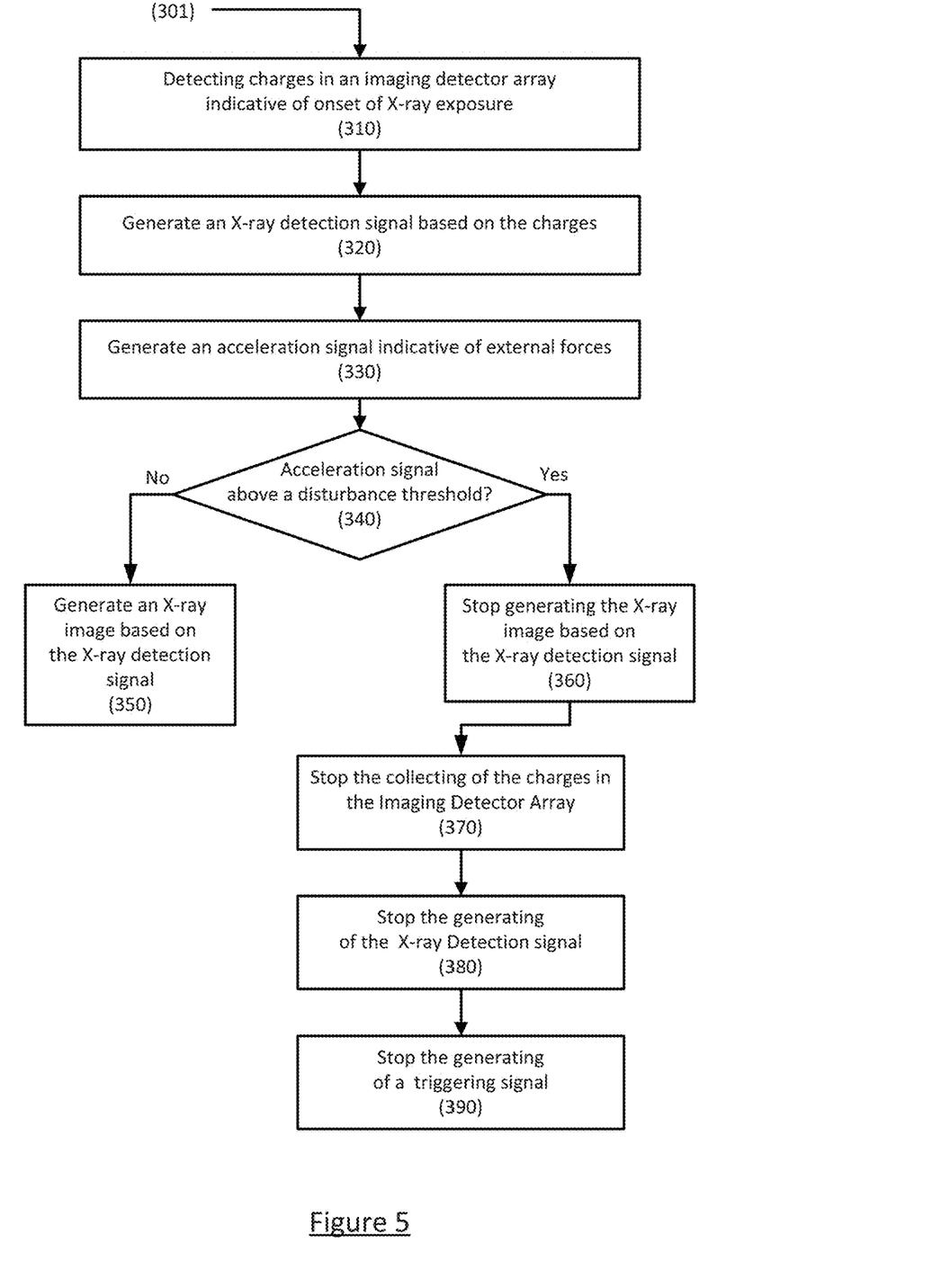
FIG. 5 shows a flow diagram illustrating one embodiment of a process for generating an X-ray image by an imaging device with bump detection, all in accordance with certain embodiments of the present disclosure.

FIG. 5 shows a flow diagram illustrating one embodiment of a process 301 for generating an X-ray image by an imaging device with bump detection, according to certain embodiments of the present disclosure. The process 301 sets forth various functional blocks or actions that may be described as processing steps, functional operations, events, and/or acts, which may be performed by hardware, software, and/or firmware. Those skilled in the art in light of the present disclosure will recognize that numerous alternatives to the functional blocks shown in FIG. 5 may be practiced in various implementations. In some embodiments, machine-executable instructions for the process 301 may be stored in memory, executed by a processing unit, and/or implemented in the imaging device 130 of FIG. 1.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments. Moreover, one or more of the outlined steps and operations may be performed in parallel.

At block 310, an imaging detector array of the imaging device may be configured to collect charges during an X-ray exposure at the imaging detector array. The X-ray exposure may be caused by an X-ray generator emitting X-rays toward the imaging device.

At block 320, a signal generator of the imaging device may be configured to generate an X-ray detection signal based on the charges collected by the imaging detector array.

At block 330, an accelerometer of the imaging device may be configured to generate an acceleration signal indicative of external forces applied to the imaging device.

At block 340, a signal processor of the imaging device may determine whether the acceleration signal is below a predetermined disturbance threshold. If the determination at block 340 is "No", the process 301 may proceed to block 350. If the determination at block 340 is "Yes", the process 301 may proceed to block 360.

At block 350, the signal processor of the imaging device may further determine whether the X-ray detection signal exceeds a predetermined X-ray threshold. If this determination returns "Yes," the signal processor may generate the X-ray image based on the X-ray detection signal, and the process 301 may terminate. If this determination returns "No", then the process 301 may also terminate.

At block 360, the signal processor may stop the generation of the X-ray image based on the X-ray detection signal, if the signal processor is in the process of performing operations of block 350.

At block 370, the signal processor may transmit an interrupt signal to the imaging detector array to temporarily stop the collecting of the charges for a fixed amount of time.

At block 380, in response to a determination that the X-ray detection signal exceeds a predetermined X-ray threshold, the signal processor may transmit an interrupt signal to the signal generator to temporarily stop the generation of the X-ray detection signal for a fixed amount of time.

At block 390, a current detector of the imaging device may be configured to generate a triggering signal indicative of existence of the X-ray exposure at the imaging detector array and trigger the signal generator to initiate the generation of the X-ray detection signal. The signal processor may transmit an interrupt signal to the current detector of the imaging device to temporarily stop the generation of the triggering signal for a fixed amount of time. In some embodiments, the signal processor may further transmit an interrupt signal to the current detector to prevent the triggering signal from initiating the generation of the X-ray detection signal by the signal generator. Alternatively, the signal processor may transmit an interrupt signal to delay (e.g., for a duration of typical external bumps) the current detector 133 from triggering the signal generator 134 to initiate the generation of the X-ray detection signal.

In some embodiments, the signal processor may transmit an interrupt signal to the X-ray generator to temporarily stop generating an X-ray toward the imaging detector array, which would result in the X-ray exposure at the imaging detector array for a fixed amount of time. Further, the x-ray generator may adjust a duration or intensity of the X-ray exposure based on a sensitivity of pixels in the imaging detector array or delays by the signal processor.

Thus, methods and systems for generating an X-ray image by an imaging device with bump detection have been described. The techniques introduced above can be implemented in special-purpose hardwired circuitry, in software and/or firmware in conjunction with programmable circuitry, or in a combination thereof. Special-purpose hardwired circuitry may be in the form of, for example, one or more application-specific integrated circuits (ASICs), programmable logic devices (PLDs), field-programmable gate arrays (FPGAs), and others.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. Those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

Software and/or firmware to implement the techniques introduced here may be stored on a non-transitory machine-readable storage medium and may be executed by one or more general-purpose or special-purpose programmable microprocessors. A "machine-readable storage medium", as the term is used herein, includes any mechanism that provides (i.e., stores and/or transmits) information in a form accessible by a machine (e.g., a computer, network device, personal digital assistant (PDA), mobile device, manufacturing tool, any device with a set of one or more processors, etc.). For example, a machine-readable storage medium includes non-transitory recordable/non-recordable media (e.g., read-only memory (ROM), random access memory (RAM), magnetic disk storage media, optical storage media, flash memory devices, etc.)

Although the present disclosure has been described with reference to specific exemplary embodiments, it will be recognized that the disclosure is not limited to the embodiments described, but can be practiced with modification and alteration without departing from the principles and concepts of this disclosure and claims. Accordingly, the specification and drawings are to be regarded in an illustrative sense rather than a restrictive sense.

We claim:

1. An imaging device for generating an X-ray image, comprising:
   an imaging detector array configured to collect charges during an X-ray exposure at the imaging detector array;
   a signal generator coupled with the imaging detector array, wherein the signal generator is configured to generate an X-ray detection signal based on the charges collected by the imaging detector array and read out by the signal generator;
   an accelerometer configured to generate an acceleration signal indicative of external forces applied to the imaging device; and
   a signal processor coupled with the signal generator and the accelerometer, wherein the signal processor;
      provides a first delay of a triggering signal from generating the X-ray detection signal to allow the accelerometer to generate the acceleration signal, wherein the triggering signal is indicative of existence of the X-ray exposure at the imaging detector array; and
   is configured to, in response to a determination that the acceleration signal is below a predetermined disturbance threshold and the X-ray detection signal exceeds a predetermined X-ray threshold, generate the X-ray image based on the X-ray detection signal, and
   wherein in response to a determination that the acceleration signal exceeds the predetermined disturbance threshold and the X-ray detection signal exceeds the predetermined X-ray threshold:
      the signal processor is further configured to stop the generating of the X-ray image based on the X-ray detection signal when the signal processor is in the process of generating the X-ray image based on the X-ray detection signal; or
      the signal processor is further configured to transmit an interrupt signal to the imaging detector array to stop the collecting of the charges; or
      the signal processor is further configured to transmit an interrupt signal to the signal generator to stop the generating of the X-ray detection signal for a fixed amount of time; or
      the signal processor is further configured to provide a second delay of the triggering signal from triggering the signal generator to initiate the generating of the X-ray detection signal until after a duration of the external forces.

2. The imaging device as recited in claim 1, further comprising:
   a current detector coupled with the imaging detector array, wherein the current detector is configured to trigger the signal generator to initiate the generating of the X-ray detection signal by generating the triggering signal.

3. The imaging device as recited in claim 2, wherein in response to the determination that the acceleration signal exceeds the predetermined disturbance threshold, the signal processor is further configured to transmit an interrupt signal to the current detector to stop the generating of the triggering signal.

4. The imaging device as recited in claim 1, further comprising:
   an X-ray generator coupled with the imaging detector array, wherein the X-ray generator is configured to emit an X-ray toward the imaging detector array resulting in the X-ray exposure at the imaging detector array, and in response to the determination that the acceleration signal exceeds the predetermined disturbance threshold, the signal processor is further configured to transmit an interrupt signal to the X-ray generator to temporarily stop the generating of the X-ray for a fixed amount of time.

5. The imaging device as recited in claim 1, further comprising:
   an indicator coupled with the accelerometer, wherein in response to the determination that the acceleration signal exceeds the predetermined disturbance threshold, the signal processor is further configured to activate the indicator.

6. The imaging device as recited in claim 1, wherein the predetermined disturbance threshold is at least 250 mG.

7. The imaging device as recited in claim 1, wherein the interrupt signal includes at least one of an analog signal or a digital signal that instructs the imaging detector array to temporarily stop the collecting of the charges for a specified time period.

8. The imaging device as recited in claim 1, wherein in response to a determination that the acceleration signal exceeds the predetermined disturbance threshold, the signal processor is further configured to transmit an interrupt signal to a current detector of the imaging device to switch the imaging detector array, the signal generator, or a signal generator into a low-power mode.

9. A method for generating an X-ray image by an imaging device, comprising:
  collecting, by an imaging detector array of the imaging device, charges during an X-ray exposure at the imaging detector array;
  generating, by a signal generator of the imaging device, an X-ray detection signal based on the charges collected by the imaging detector array and read out by the signal generator;
  generating, by an accelerometer of the imaging device, an acceleration signal indicative of external forces applied to the imaging device;
  delaying by a first delay, by a signal processor of the imaging device, a triggering signal from generating the X-ray detection signal to allow the accelerometer to generate the acceleration signal, wherein the triggering signal is indicative of existence of the X-ray exposure at the imaging detector array;
  in response to a determination that the acceleration signal is below a predetermined disturbance threshold and the X-ray detection signal exceeds a predetermined X-ray threshold, generating, by the signal processor of the imaging device, the X-ray image based on the X-ray detection signal; and
  in response to a determination that the acceleration signal exceeds the predetermined disturbance threshold and the X-ray detection signal exceeds the predetermined X-ray threshold:
    stopping, by the signal processor, the generating of the X-ray image based on the X-ray detection signal when the signal processor is in the process of generating the X-ray image based on the X-ray detection signal; or
    transmitting, by the signal processor, an interrupt signal to the imaging detector array to stop the collecting of the charges; or
    transmitting, by the signal processor, an interrupt signal to the signal generator to stop the generating of the X-ray detection signal; or
    transmitting, by the signal processor, an interrupt signal to the current detector to provide a second delay of the triggering signal from triggering the signal generator to initiate the generating of the X-ray detection signal until after a duration of the external forces.

10. The method as recited in claim 9, further comprising:
  in response to the determination that the acceleration signal exceeds the predetermined disturbance threshold, transmitting, by the signal processor, an interrupt signal to a current detector of the imaging device to stop generating a triggering signal indicative of existence of the X-ray exposure at the imaging detector array.

11. The method as recited in claim 9, further comprising:
  in response to the determination that the acceleration signal exceeds the predetermined disturbance threshold, transmitting, by the signal processor, an interrupt signal to an X-ray generator to temporarily stop generating an X-ray toward the imaging detector array resulting in the X-ray exposure at the imaging detector array for a fixed amount of time.

12. The method as recited in claim 11, wherein the generating of the X-ray comprises:
  adjusting, by the X-ray generator, a duration of the X-ray exposure based on a sensitivity of pixels in the imaging detector array or delays by the signal processor.

13. The method as recited in claim 9, further comprising:
  in response to the determination that the acceleration signal exceeds the predetermined disturbance threshold, transmitting, by the signal processor, an interrupt signal to a current detector of the imaging device to switch the imaging detector array, the signal generator, or a signal generator into a low-power mode.

14. An imaging device for generating an X-ray image, comprising:
  an imaging detector array configured to collect charges during an X-ray exposure at the imaging detector array;
  a signal generator coupled with the imaging detector array, wherein the signal generator is configured to generate an X-ray detection signal based on the charges collected by the imaging detector array and read out by the signal generator;
  an accelerometer configured to generate an acceleration signal indicative of external forces applied to the imaging device; and
  a signal processor coupled with the signal generator and the accelerometer, wherein the signal processor:
    provides a first delay of a triggering signal from generating the X-ray detection signal to allow the accelerometer to generate the acceleration signal, wherein the triggering signal is indicative of existence of the X-ray exposure at the imaging detector array; and
    is configured to, in response to a determination that the acceleration signal is below a predetermined disturbance threshold and the X-ray detection signal exceeds a predetermined X-ray threshold, generate the X-ray image based on the X-ray detection signal, and
  wherein in response to a determination that the acceleration signal exceeds the predetermined disturbance threshold and the X-ray detection signal exceeds the predetermined X-ray threshold:
  the signal processor is further configured to provide a second delay of the triggering signal from triggering the signal generator to initiate the generating of the X-ray detection signal until after a duration of the external forces.

* * * * *